US011576855B2

(12) United States Patent
Padmanabhan et al.

(10) Patent No.: US 11,576,855 B2
(45) Date of Patent: *Feb. 14, 2023

(54) EFFERVESCENT COMPOSITION AND METHOD OF MAKING IT

(71) Applicant: STEERLIFE INDIA PRIVATE LIMITED, Bangalore (IN)

(72) Inventors: Babu Padmanabhan, Bangalore (IN); Rakshit Shetty, Bangalore (IN); Vijay Kulkarni, Bangalore (IN); Himadri Sen, Pune (IN); Indu Bhushan, Bangalore (IN)

(73) Assignee: STEERLIFE INDIA PRIVATE LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/445,918

(22) Filed: Aug. 25, 2021

(65) Prior Publication Data

US 2022/0192973 A1   Jun. 23, 2022

Related U.S. Application Data (62) Division of application No. 15/512,515, filed as application No. PCT/IB2015/000400 on Mar. 26, 2015, now abandoned.

(30) Foreign Application Priority Data

Sep. 17, 2014   (IN) ............................ 4527/CHE/2014

(51) Int. Cl.
| | |
|---|---|
| *A61K 9/46* | (2006.01) |
| *A61K 31/546* | (2006.01) |
| *A61K 9/16* | (2006.01) |
| *A61K 45/06* | (2006.01) |
| *A61K 9/00* | (2006.01) |
| *A61K 9/20* | (2006.01) |
| *A61K 31/198* | (2006.01) |
| *A61K 31/616* | (2006.01) |

(52) U.S. Cl.
CPC .......... *A61K 9/0007* (2013.01); *A61K 9/0053* (2013.01); *A61K 9/1611* (2013.01); *A61K 9/1617* (2013.01); *A61K 9/1682* (2013.01); *A61K 9/1694* (2013.01); *A61K 9/2009* (2013.01); *A61K 9/2013* (2013.01); *A61K 31/198* (2013.01); *A61K 31/546* (2013.01); *A61K 31/616* (2013.01); *A61K 45/06* (2013.01)

(58) Field of Classification Search
CPC ............................ A61K 9/0007; A61K 9/1694
See application file for complete search history.

(56) References Cited

U.S. PATENT DOCUMENTS

| | | | |
|---|---|---|---|
| 1,450,865 | A | 4/1923 | Pelc |
| 2,071,841 | A | 2/1937 | Alfred |
| 2,851,361 | A | 9/1958 | Diller |
| 2,988,562 | A | 6/1961 | Weinmayr |
| 3,663,271 | A | 5/1972 | Gergely |
| 3,773,922 | A | 11/1973 | Gergely et al. |
| 4,004,036 | A | 1/1977 | Schmitt |
| 4,252,664 | A | 2/1981 | Inamorato |
| 4,305,502 | A | 12/1981 | Gergely et al. |
| 4,371,516 | A | 2/1983 | Gregory et al. |
| 4,614,648 | A | 9/1986 | Bru |
| 4,678,661 | A | 7/1987 | Gergely et al. |
| 4,824,664 | A | 4/1989 | Tarral et al. |
| 5,019,302 | A | 5/1991 | Sparks et al. |
| 5,055,306 | A | 10/1991 | Barry et al. |
| 5,188,825 | A | 2/1993 | Iles et al. |
| 5,223,246 | A | 6/1993 | Kondo et al. |
| 5,178,878 | A | 12/1993 | Wehling et al. |
| 5,302,396 | A | 4/1994 | Phadke et al. |
| 5,529,789 | A | 6/1996 | Lo |
| 5,631,023 | A | 5/1997 | Kearney et al. |
| 5,667,807 | A | 9/1997 | Huerner et al. |
| 5,738,875 | A | 4/1998 | Yarwood et al. |

(Continued)

FOREIGN PATENT DOCUMENTS

| | | |
|---|---|---|
| CA | 2331671 | 1/2008 |
| CN | 102860302 A | 1/2013 |

(Continued)

OTHER PUBLICATIONS

Citric acid, Sigma-Aldrich, 2022 (Year: 2022).*
Non-Final Office Action received for U.S. Appl. No. 15/781,090, dated Oct. 9, 2020, 12 pages.
PCT Search Report and Written Opinion for PCT/IB2016/057530, dated Mar. 23, 2017.
European Pharmacopoeia 7.0, published 2010, pp. 714, 727, and 737.
International Search Report and Written Opinion received in PCT Application No. PCT/IB2015/000400, dated Aug. 31, 2015, 13 pages.

(Continued)

*Primary Examiner* — Robert A Wax
*Assistant Examiner* — William Craigo
(74) *Attorney, Agent, or Firm* — Oliff PLC (57) ABSTRACT

The present disclosure concerns effervescent compositions and methods of making and using the same. In some embodiments, the disclosed effervescent compositions are formed from an input blend comprising an acid and a base by granulating the input blend in a twin-screw processor. The granules formed from the input blend can be formed by an in situ granulating agent, which can be a portion of the acid that melts during granulation. In some embodiments, the effervescent compositions can be made using a twin-screw processor comprising an intake zone for receiving an input blend comprising an acid and a base; a granulation initiation zone for melting only a portion of the acid to serve as an in situ granulating agent; a granulation completion zone for granulating the input blend; and an outlet for discharging the granules.

11 Claims, 2 Drawing Sheets

(56) References Cited

U.S. PATENT DOCUMENTS

| | | | |
|---|---|---|---|
| 5,750,061 A | 5/1998 | Farina et al. | |
| 5,792,473 A | 8/1998 | Gergely et al. | |
| 5,827,541 A | 10/1998 | Yarwood et al. | |
| 5,969,181 A | 10/1999 | Joerg et al. | |
| 5,976,577 A | 11/1999 | Green et al. | |
| 6,024,981 A | 2/2000 | Khankari et al. | |
| 6,071,539 A | 6/2000 | Robinson et al. | |
| 6,190,697 B1 | 2/2001 | Gergely et al. | |
| 6,221,392 B1 | 4/2001 | Khankari et al. | |
| 6,269,615 B1 | 8/2001 | Amborn et al. | |
| 6,426,111 B1 * | 7/2002 | Hirsch | A23L 2/40 426/477 |
| 6,440,926 B1 | 8/2002 | Spadoni et al. | |
| 6,488,961 B1 | 12/2002 | Robinson et al. | |
| 6,544,551 B1 | 4/2003 | Engel et al. | |
| 6,649,186 B1 | 11/2003 | Robinson et al. | |
| 6,683,043 B1 * | 1/2004 | Dovey | C11D 3/0052 510/513 |
| 6,764,601 B1 | 7/2004 | Levy et al. | |
| 7,208,175 B2 | 4/2007 | Schroeder et al. | |
| 7,507,396 B2 | 3/2009 | Aldritt et al. | |
| 7,910,030 B2 | 3/2011 | Jean-Paul et al. | |
| 7,964,212 B2 | 6/2011 | McCallister et al. | |
| 7,972,623 B2 | 7/2011 | Gergely et al. | |
| 8,329,196 B2 | 12/2012 | Jacobi et al. | |
| 8,449,906 B2 | 5/2013 | McCallister et al. | |
| 8,545,879 B2 | 10/2013 | Burns et al. | |
| 8,545,881 B2 | 10/2013 | Venkatesh et al. | |
| 8,637,076 B2 | 1/2014 | Habib et al. | |
| 9,205,054 B2 | 12/2015 | Gruber et al. | |
| 2001/0006677 A1 | 7/2001 | McGinity et al. | |
| 2001/0041165 A1 | 11/2001 | Katdare et al. | |
| 2003/0003147 A1 | 1/2003 | Katdare et al. | |
| 2003/0170301 A1 | 9/2003 | Wehling | |
| 2004/0137058 A1 | 7/2004 | Katdare et al. | |
| 2004/0265375 A1 | 12/2004 | Platteeuw et al. | |
| 2004/0265380 A1 * | 12/2004 | Delmas | A61P 5/00 424/466 |
| 2006/0008521 A1 | 1/2006 | Yeli et al. | |
| 2006/0034921 A1 | 2/2006 | Katdare et al. | |
| 2006/0134195 A1 | 6/2006 | Fu et al. | |
| 2006/0240103 A1 | 10/2006 | McCallister et al. | |
| 2008/0031825 A1 | 2/2008 | Chen et al. | |
| 2008/0187558 A1 | 8/2008 | Jacobi et al. | |
| 2010/0021393 A1 | 1/2010 | Chen et al. | |
| 2010/0034889 A1 | 2/2010 | Rau et al. | |
| 2010/0172981 A1 | 7/2010 | Gruber et al. | |
| 2011/0039293 A1 | 2/2011 | Hernandez Sierra | |
| 2011/0281008 A1 | 11/2011 | Gootenilleke et al. | |
| 2011/0287114 A1 | 11/2011 | Johnson | |
| 2012/0009129 A1 | 1/2012 | Brzeczko | |
| 2013/0028844 A1 | 1/2013 | Bilgic | |
| 2013/0217777 A1 | 8/2013 | Kirkorian | |
| 2013/0287706 A1 | 10/2013 | Hayward et al. | |
| 2014/0066413 A1 | 3/2014 | Howard et al. | |
| 2018/0360737 A1 | 12/2018 | Bhushan et al. | |

FOREIGN PATENT DOCUMENTS

| | | |
|---|---|---|
| CN | 102823622 B | 12/2013 |
| CN | 102823589 B | 6/2014 |
| DE | 102012102414 | 10/2013 |
| EP | 203768 B2 | 5/1993 |
| EP | 711560 B1 | 6/2001 |
| EP | 1404296 B1 | 4/2004 |
| EP | 2649989 | 10/2013 |
| GB | 1338071 A | 11/1973 |
| GB | 2307857 A | 11/1999 |
| IN | 1522/DEL/2010 | 1/2012 |
| JP | 2004016148 A | 5/2006 |
| KR | 10-2014-0131205 | 11/2014 |
| WO | WO 1997/025030 A1 | 7/1997 |
| WO | WO 1998/003088 A2 | 1/1998 |
| WO | WO 1998/46715 | 10/1998 |
| WO | WO 99/43306 A1 | 9/1999 |
| WO | WO 2000/034422 A2 | 6/2000 |
| WO | WO 2001/80822 | 11/2001 |
| WO | WO 02/069932 A1 | 9/2002 |
| WO | WO 2002/098388 | 12/2002 |
| WO | WO 2003/017986 A1 | 3/2003 |
| WO | WO 2002/05820 | 4/2003 |
| WO | WO 1999/59553 | 8/2003 |
| WO | WO 2004/047974 A1 | 6/2004 |
| WO | WO 2006/092711 | 9/2006 |
| WO | WO 2007/038979 | 4/2007 |
| WO | WO 2007/065441 A1 | 6/2007 |
| WO | WO 2007/098924 | 9/2007 |
| WO | WO 2009/071954 | 6/2009 |
| WO | WO2011/139251 | 11/2011 |
| WO | WO 2010/117346 | 2/2012 |
| WO | WO 2012/064306 A2 | 5/2012 |
| WO | WO 2013/077822 | 5/2013 |

OTHER PUBLICATIONS

Repka, "Hot-Melt Extrusion," American Pharmaceutical Review, Russell Publishing, vol. 12, No. 6, Oct. 1, 2009, pp. 18-27, 10 pages.

Haack et al., TOPO Granulation Technology, TechnoPharm 2, Nr. 3, 186-191, 2012.

J. Amela et al., "Methods for the Determination of the Carbon Dioxide Evolved From Effervescent Systems," Drug Development and Industrial Pharmacy, 19(9), 1019-1036, 1993.

Crowley et al., "Pharmaceutical Applications of Hot-Melt Extrusion: Part I," Drug Development and Industrial Pharmacy, 33:909-926, 2007.

M. Maniruzzaman et al., "A Review of Hot-Melt Extrusion: Process Technology to Pharmaceutical Products," International Scholarly Research Network ISRN Pharmaceutics vol. 2012, Article ID 436763, 9 pages, 2012.

Aslani et al., "Formulation, Characterization and Physicochemical Evaluation of Potassium Citrate Effervescent Tablets," Advanced Pharmaceutical Bulletin, 2013, 3(1), 217-225.

Reddy et al., "Conventional and Patented Technologies in oral dispersible tablets: A Review," Journal of Chemical and Pharmaceutical Sciences, vol. 6, issue 4, pp. 286-292, 2013, 7 pages.

McLaughlin et al., "Orally Disintegrable Tablets the Effect of Recent FDA Guidance on ODT Technology and Applications," Pharmaceutical Technology, Sep. 2009 issue, 8 pages.

Dejan Djuric, "Continuous Granulation with a Twin-Screw Extruder," Dissertation by Dejan Djuric, Germany, Jun. 2008, 112 pages.

Hancock et al., "The Relative Densities of Pharmaceutical Powders, Blends, Dry Granulations and Immediate release tablets," Pharmaceutical Technology, Apr. 2003, pp. 64-78.

MD Tousey, "The Granulation Process 101 Basic Technologies for Tablet Making," Pharmaceutical Technology Tableting and Granulation, 2002, pp. 9-13.

Carr, "Classifying Flow Properties of Solids," Chemical Engineering, 72(2), pp. 69-72, Feb. 1, 1965.

Carr, "Evaluating Flow Properties of Solids," Chemical Engineering, 72(1 ), pp. 163-168, Jan. 18, 1965.

Hausner, "Friction Conditions in a Mass of Metal Powder," International Journal of Powder Metallurgy, 3(4): 7 pages, 1967.

Podczeck, International Journal of Pharmaceutics, 142, 1996 (Year: 1996).

* cited by examiner

EFFERVESCENT COMPOSITION AND METHOD OF MAKING IT

RELATED APPLICATIONS

This application is a divisional of co-pending U.S. patent application Ser. No. 15/512,515, filed Mar. 17, 2017, which is the United States National Phase application under 35 U.S.C. § 371 of International PCT Patent Application No. PCT/IB2015/000400, filed Mar. 26, 2015, which claims priority to Indian Patent Application No. 4527/CHE/2014, filed Sep. 17, 2014, the entire contents of each of which is incorporated by reference herein.

FIELD

The present disclosure relates to embodiments of effervescent compositions and methods of making and using the same.

BACKGROUND

Effervescent compositions that produce effervescence when added to water find use in pharmaceutical, food, veterinary, nutraceutical, horticultural, household, culinary, pesticidal, agricultural, cosmetic, herbicidal, industrial, cleansing, confectionery and flavoring applications. Effervescent compositions, particularly in pharmaceutical applications, are an interesting dosage form offering some unique advantages such as administration of an Active Pharmaceutical Ingredient (API) in solution form and taste masking of the API. Patients benefited by the use of effervescent tablets are the geriatric population, pediatric population and a large adult population with a gag reflex and/or swallowing difficulty. Additionally, since the API is administered as a solution, problems associated with dissolution, that is, absorption rate and extent of bioavailability are minimized and a rapid on-set of action can be realized.

Manufacture of effervescent compositions is complicated requiring careful environmental control on account of the tendency of effervescent compositions to become reactive in the presence of moisture. This reaction is auto-catalyzed and is difficult to control. Also, effervescent compositions require rapid disintegration times which depend on the porosity of the composition. For example, effervescent tablets require rapid disintegration times of generally less than 60 seconds. At the same time, effervescent compositions also need to be amenable to packaging and transportation. For example, effervescent tablets need to have adequate hardness so that they can be satisfactorily packed and transported. Finally, effervescent compositions should evolve sufficient amount of carbon dioxide in water to be effective. Various methods have been explored for the manufacture of effervescent compositions such as wet granulation, dry granulation, direct compression and hot melt processing. The effervescent compositions resulting from these conventional techniques however suffer from one or more of disadvantages such as low carbon dioxide ($CO_2$) content, low porosity and longer disintegration times, for example, when external binders are used, granules that are not free flowing, or are difficult to compress and form tablets, low mechanical strength, difficulty in manufacturing and the like.

Therefore, there is a need for effervescent compositions that have high carbon dioxide retention, high porosity and high mechanical strength and which do not require affirmatively adding a granulating agent and/or a binder. There is also a need for a process for manufacture of such effervescent compositions which is rapid and can be easily controlled. It is desirable that such a process be continuous.

SUMMARY

The present disclosure relates to a granular composition comprising an anhydrous acid component comprising a combination of a portion of the acid that has been melted and a portion of the acid that has not been melted and; an anhydrous base component comprising a carbonate functional group, wherein the base component is capable of reacting with the acid component to form carbon dioxide; and wherein the anhydrous acid component and the anhydrous base component are present in a weight ratio ranging from 1:9 to 9:1 and the composition does not comprise an affirmatively added granulating agent.

The present disclosure also relates to a porous effervescent composition formed from an input blend comprising an acid and a base by granulating the input blend in a twin-screw processor, the porous effervescent composition comprising granules formed by an in situ granulating agent, wherein the in situ granulating agent is a portion of the acid, the portion of the acid being a portion of the acid that melts during granulation.

The present disclosure also concerns an oral solid dosage form such as an effervescent tablet or a powder for oral administration or a combination, the oral solid dosage form comprising a porous effervescent composition formed from an input blend comprising an acid and a base by granulating the input blend in a twin-screw processor, the porous effervescent composition comprising granules formed by an in situ granulating agent, wherein the in situ granulating agent is a portion of the acid, the portion of the acid being a portion of the acid that melts during granulation; and one or more optional processing excipients.

The present disclosure further concerns a twin screw processor for preparing porous effervescent granules, the processor comprising an intake zone for receiving an input blend comprising an acid and a base; a granulation initiation zone for melting only a portion of the acid to serve as an in situ granulating agent; a granulation completion zone for granulating the input blend; and an outlet for discharging the granules.

The present disclosure further concerns a process for preparing porous effervescent granules, the process comprising feeding an input blend comprising an acid and a base into a twin-screw processor; melting only a portion of the acid to serve as an in situ granulating agent; granulating the input blend to form granules; and optionally collecting the granules from the twin screw processor.

The present disclosure further concerns porous effervescent granules comprising an acid and a base, wherein the granules have porosity at least 50% greater than the porosity of an input blend used to prepare the granules and the granules retain at least 90% of carbon dioxide of the input blend.

DETAILED DESCRIPTION

I. Explanation of Terms

The following explanation of terms is provided to better describe the present disclosure and to guide those of ordinary skill in the art in the practice of the present disclosure. As used herein, "comprising" means "including but not limited to" and the singular forms "a" or "an" or "the" include plural references unless the context clearly dictates otherwise. The term "or" refers to a single element of stated alternative elements or a combination of two or more elements, unless the context clearly indicates otherwise.

The devices, compositions, and methods described herein should not be construed as limiting in any way. Instead, the present disclosure is directed towards all novel and non-obvious features and aspects of the various disclosed embodiments, alone and in various combinations and sub-combinations with one another. The disclosed devices, compositions, and methods are not limited to any specific aspect or feature or combinations thereof, nor do the disclosed devices, compositions, and methods require that any one or more specific advantages be present or problems be solved. Any theories of operation are to facilitate explanation, but the disclosed devices, compositions, and methods are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed devices, compositions, and methods can be used in conjunction with other devices, compositions, and methods. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections. Examples are described with reference to directions indicated as "above," "below," "upper," "lower," and the like. These terms are used for convenient description, but do not imply any particular spatial orientation.

Unless explained otherwise, all technical and scientific terms used herein have the same meaning as commonly understood to one of ordinary skill in the art to which this disclosure belongs. Unless otherwise indicated, all numbers expressing quantities of components, molecular weights, percentages, temperatures, times, and so forth, as used in the specification or claims are to be understood as being modified by the term "about". Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

II. Overview

The present disclosure relates to a porous effervescent composition, more specifically, granules. The composition possesses one or more critical attributes such as the ability to flow freely, compressibility, porosity, significant amount of retained carbon dioxide and mechanical strength. The effervescent compositions in the form of granules can be used as such, can be mixed with other excipients before being used or are suitable for example for forming effervescent tablets with desired mechanical strength, effectiveness and rapid disintegration times. In some embodiments, the porous effervescent compositions in the form of granules of this disclosure have porosity at least 50% greater than the porosity of the input blend and retain all or substantially all of the carbon dioxide ($CO_2$) content of the input blend. Herein, the porosity of the effervescent composition with respect to the input blend is referred to as relative porosity. The relative porosity may be measured either as the relative bulk porosity or the relative tap porosity. The term "all or substantially all of the $CO_2$ content of the input blend" means at least 90% of the $CO_2$ content of the input blend and is also expressed as the percent relative retained $CO_2$ content of the composition, specifically, granules.

Effervescence in effervescent compositions is obtained due to the presence of acid and base substances such as carbonates or bicarbonates that react rapidly in the presence of water and release $CO_2$ to provide a carbonated or sparkling liquid drink. Due to liberation of $CO_2$, the dissolution of API in water as well as taste masking of the API is achieved.

Manufacture of satisfactory effervescent compositions requires a balance of the porosity of the composition, amount of carbon dioxide retained in the composition and the mechanical strength of the composition.

One conventional technique for producing effervescent compositions is wet granulation. Wet granulation requires addition or generation of a granulating agent (other than the in situ granulating agent disclosed herein). The affirmatively added granulating agent can be water, steam, or solvents such as alcohol, propylene glycol or glycerin that act as moistening agents or a binding agent such as polyvinylpyrrolidone. One type of wet granulation preferred for making effervescent formulations is TOPO vacuum granulation in which a small amount of water is added during the process. Additional water is generated during the chain reaction initiated by the reaction of citric acid with bi-carbonates or carbonates. To control and manage this chain reaction, water is eliminated by repeatedly applying a vacuum for certain periods of time during the granulation process. Porosity of such compositions is a result of the carbon dioxide generated during the reaction. Control of this process is very critical. The porosity and carbon dioxide content of compositions may vary depending on the extent of the reaction.

A fluid bed spray granulator can also be used for wet granulation where granulation and drying take place at the same time. Although a low moisture level is attained throughout the process, a large volume of granulation fluid is needed thereby making the process longer and expensive to perform with a potential risk of loss of effervescence quality.

Wet granulation may also be carried out by fusion method. In this method, alkali is mixed with acid, which is at least partially a hydrated acid. The mixture is heated until the water of crystallization is released. The released water of crystallization then acts as a granulating agent. Although this method avoids use of external water as granulating agent, the method can also trigger a chain reaction that is difficult to terminate leading to additional moisture that needs to be removed. Porosity of the composition is once again a result of the carbon dioxide generated in the reaction. The effervescent compositions produced by this method have variable and in some cases, lower $CO_2$ content. Also, the tablets produced from these compositions do not have sufficient mechanical strength for product handling and packaging operations.

Wet granulation may also be carried out by running two separate granulation steps for the acid and the base components with a subsequent dry blending step. A challenge in this conventional technique is achieving tablet homogeneity, as it is difficult to homogenously blend the material into a uniform composition.

Another drawback of these conventional wet granulation techniques is the fact that the use of solvents such as alcohol for wet granulation requires complex equipment such as flame proof versions of the equipment described above and higher safety requirements to handle the granulation fluid.

Another conventional method for forming effervescent compositions is dry granulation. This method generally includes slugging or roller compaction without requiring any liquid or binder. However, the compositions obtained by this method possess low porosity. Direct compression techniques have also been used for preparing effervescent compositions which have low porosity resulting in longer disintegration times and low mechanical strength.

Hot melt processing has also been employed for the manufacture of effervescent compositions and broadly involves melting of a binder. One such method is disclosed in U.S. Pat. Nos. 6,071,539, 6,488,961 and 6,649,186 to Robinson, which discuss hot melt extrusion involving melting of a binder. Although the use of binders can potentially avoid the drawbacks of using water or solvents, there are limitations on the type of binders that can be used and the resulting compositions have low porosity and $CO_2$ content. U.S. Pat. No. 6,426,111 describes another hot melt process in which the acid is melted and mixed with an alkali and other ingredients. The process ensures complete entrapment of the base and other ingredients by the melted acid, so as to form a protective layer. The taffy mass formed by this process may be directly extruded to form desired shapes. The process is limited by the excipients which need to be used to impart porosity to the composition so formed. This process, also, requires melting all acid present in the composition to achieve the results disclosed therein. Further, it does not provide effervescent tablets having improved properties and performance that is exhibited by the presently disclosed composition. The present inventors replicated the process disclosed in the U.S. Pat. No. 6,426,111 to ascertain the same. As disclosed in the patent, required quantity of anhydrous citric acid was placed in a stainless steel container and placed on a heating plate maintained at 125° C. However, there was no sign of melting of anhydrous citric acid even after exposing it to 125° C. for 45 minutes. Therefore, the temperature was increased to 145 to 150° C. The effervescent composition formed according to the process disclosed in this patent had percent relative retained $CO_2$ content of around 71.55% and relative specific bulk porosity of 14.10% only.

In contrast to these conventional methods, the present disclosure concerns a porous effervescent composition formed from an input blend comprising an acid and a base by granulating the input blend in a twin-screw processor, the composition comprising granules formed by an in situ granulating agent, wherein the in situ granulating agent is a portion of the acid, the portion of the acid being a portion of the acid that melts during granulation. The in situ granulating agent of the present disclosure is distinct from an affirmatively added granulating agent, which is a granulating agent other than (or separate from) the acid component that reacts with the base to provide effervescence.

A contribution of the present disclosure over the conventional methods described above resides in obtaining a porous effervescent composition having porosity at least 50% greater than the porosity of the input blend.

A contribution of the present disclosure over the conventional methods described above resides in obtaining a porous effervescent composition having retained carbon dioxide content of at least 90% of the input blend.

The melting of only a portion of acid leads to formation of solid bridges with the molecules of other particles. This leads to the binding of the particles in close proximity to form deformable, irregular shaped, porous granules that have improved compressibility. The melting of only a portion of the acid can provide granules suitable for tableting. Complete melting of the acid, as is described in the methods of U.S. Pat. No. 6,426,111, results in over-granulation and consequently a poor quality effervescent tablet with compromised effervescence efficiency.

As little or no reaction takes places between the acid and the base during granulation, negligible or no carbon dioxide is lost during granulation. In some embodiments, the granules retain all or substantially all of the $CO_2$ content of the input blend. This also leads to improved effervescence when exposed to water. In some embodiments, the effervescent tablets made from the granules of the present disclosure have a disintegration time of less than sixty seconds.

Further, as the acid and the base molecules are in close proximity, the granules formed according to the present disclosure exhibit improved mechanical strength. For example, tablets formed from the granules exhibit improved hardness as well as disintegration time when exposed to water.

Thus, formation of the porous effervescent composition having porosity at least 50% greater than the porosity of the input blend or retained carbon dioxide content of at least 90% of the input blend using an in situ granulating agent results in avoiding the problems associated with conventional methods (e.g., using affirmatively added granulating agents, such as water or binders, or completely melting an acid component). It further eliminates the requirement of additional steps such as drying and other processing steps providing for ease of manufacturing.

III. Compositions and Methods of Making and Using the Same

Disclosed herein are embodiments of a porous effervescent composition that exhibit improved properties contributing to the composition's use in a variety of applications. In some embodiments, the porous effervescent compositions can be formed using an input blend comprising an acid and a base. In some embodiments, the porous effervescent composition has porosity at least 50% greater than the porosity of the input blend. In some embodiments, the porous effervescent composition has retained carbon dioxide content of at least 90% of the input blend. It has been observed that an increase in porosity of the granules can be achieved without compromising with other properties of the granules.

In accordance with an exemplary embodiment, the composition does not contain, or is free of, an affirmatively added granulating agent. The composition is understood as being free of an affirmatively added component (other than the acid or base) that either deleteriously affects the function of the acid and base components and/or is an affirmatively added granulating agent (e.g., water, a binding agent, or any of the conventional granulating agents described above).

In accordance with one embodiment, the acid can be any organic acid in free acid, acid anhydride and acid salt form. Specifically, the acid can be selected from citric acid and other acids such as tartaric acid, maleic acid, fumaric acid, malic acid, adipic acid, succinic acid, lactic acid, glycolic acid, alpha hydroxy acids, ascorbic acid, amino acids and their alkali hydrogen acid salts. Mixture of one or more acids can also be used. In accordance with an embodiment, the acid is an API. Examples of such acids include aspirin, N-acetyl cysteine, ibandronic acid, ibuprofen, ketoprofen, mefenamic acid, ascorbic acid and other acidic amino acids.

In accordance with one embodiment, the base is a carbon dioxide precursor and can be selected from a carbonate-containing compound, such as carbonates; sesquicarbonates; bicarbonate salts of potassium, lithium, sodium, calcium, ammonium; L-lysine carbonate; arginine carbonate; sodium glycine carbonate; or sodium amino acid carbonate. Mixtures of one or more bases can also be used. For example, in some embodiments, the base is a mixture of sodium carbonate and sodium bicarbonate.

In some embodiments, the composition consists essentially of the acid and the base. The acid and the base are present in a quantity sufficient to cause effervescence on addition of water. The amount of the acid and the base in the composition can vary depending on the acid and the base used. In some embodiments, the amount of acid used can range from 10% w/w to 90% w/w, such as 20% w/w to 70% w/w, or 40 to 50% w/w in the composition. In exemplary embodiments, the amount of acid used can be selected from 40% w/w to 50% w/w in the composition. The amount of the base can range from 10% w/w to 90% w/w, such as 20% w/w to 70% w/w, or 45% to 55% w/w in the composition. In exemplary embodiments, the amount of the base used can be selected from 45% to 55% w/w in the composition. In some embodiments, the molar ratio of the acid and the base can vary depending on the desired pH maintenance of the solution during effervescence. In exemplary embodiments, the molar ratio of the acid and the base can be selected from 3:1 to 1:5. In exemplary embodiments, the weight ratio of the acid and the base can be selected from 1:9 to 9:1.

In one embodiment, the ingredients of the input blend are anhydrous. In accordance with an exemplary embodiment, an anhydrous form of the acid is used to ensure that no water of crystallization is released when the acid is heated in the granulation initiation zone of the twin screw processor. In accordance with an exemplary embodiment, the anhydrous form of the base is used. In yet another embodiment, both an anhydrous form of the acid and an anhydrous form of the base can be used. In accordance with another embodiment, the input blend has moisture content of less than 0.5%. One or more of the ingredients of the input blend can be subjected to a moisture removal step before feeding into the processor. In some embodiments, it can be beneficial to maintain the moisture content of the acid and the base at less than 0.25% w/w. The moisture of the acid and the base may be removed by any drying method known to those of ordinary skill in the art. For example, moisture can be removed by tray drying of the ingredients at 45 to 60° C. The ingredients can then be sieved to obtain fine particles for homogeneous processing. In some embodiments, the ingredients are subjected to sieving through ASTM #40 and/or #60 mesh sieve to obtain particles having size less than 420 microns and 250 microns respectively.

In some embodiments, the input blend can also comprise one or more active ingredients selected from pharmaceutical, food, veterinary, nutraceutical, horticultural, household, culinary, pesticidal, agricultural, cosmetic, herbicidal, industrial, cleansing, confectionery and flavoring agents, or combinations thereof.

The pharmaceutical agent includes any API covering complete range of therapeutic indications such as anti-infectives, antibacterials, antihistamines and decongestants, antiinflammatory agents, antiparasitics, antivirals, antifungal, amoebicidal, or trichomonocidal agents, analgesics, antiarthritics, antiasthmatics, anticoagulants, anticonvulsants, antidepressants, antidiabetics, antineoplastics, antipsychotics, antihypertensives, expectorants, electrolytes, laxatives, phytopharmaceuticals, muscle relaxants, diuretics and the like. The amount of the API may vary depending on the desired application and may be, for example, a unit dose based on the clinically established efficacy. For example, the amount of API can range from 0.01 mg to about 1000 mg based on the API selected.

In some embodiments, one or more API is added during the formation of the effervescent composition. In an alternate embodiment, the API is added subsequent to the formation of the effervescent composition.

The input blend can further comprise one or more processing excipients selected from soluble and insoluble lubricants, flavoring substances, coloring agents, or combinations thereof.

Soluble lubricants can include but are not limited to polyethylene glycols (PEG), for example—PEG 4000, PEG 6000 and PEG 8000, polyoxyethylene stearate and sodium or magnesium lauryl sulphate, sodium benzoate, L-leucine and the like and combinations thereof. Insoluble lubricants can include but are not limited to magnesium stearate, stearic acid, glyceryl palmitostearate and the like and combinations thereof. The amount of the lubricant depends on the lubricating effects desired and is well known to those of ordinary skill in the art.

The flavoring substances can include but are not limited to synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, cassia oil and the like. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired.

Useful coloring agents can include but are not limited to food, drug and cosmetic (FD&C) colors, for example—dyes, pigments, lakes, natural colorants and derived colorants and natural colorants. Useful lakes include dyes adsorbed on aluminum hydroxide and other suitable carriers. Examples of suitable colors include FD&C Red No. 3, FD&C Red No. 40, FD&C Blue No. 1, FD&C Blue No. 2, FD&C Yellow No. 5, FD&C Yellow No. 6, FD&C Green No. 3 and combinations thereof. The amount of coloring agent depends on the aesthetic appearance desired and is well known to those skilled in the art.

The present disclosure also concerns an oral solid dosage form comprising the porous effervescent composition described above. Examples of the oral solid dosage form include but are not limited to an effervescent tablet, a powder for oral administration, or combinations thereof. The term effervescent tablet also includes variants thereof such as an orally disintegrating tablet and a rapidly disintegrating tablet which utilize effervescence to achieve the desired results.

The oral solid dosage form comprises the porous effervescent composition formed from an input blend comprising an acid and a base by granulating the input blend in a twin-screw processor, the composition comprising granules formed by an in situ granulating agent, wherein the in situ granulating agent is a portion of the acid, the portion of the acid being the portion of the acid that has been melted during granulation; and optionally, processing excipients.

The processing excipients may be selected from non-effervescent disintegrants, soluble and insoluble lubricants, flavoring substances, coloring agents, or combinations thereof.

Non-limiting examples of non-effervescent disintegrants include microcrystalline cellulose, crospovidone, starches, modified starches, clays such as bentonite, gums such as pectin, tragacanth, alginates, sodium starch glycolate and croscarmellose sodium. The amount of non-effervescent disintegrants may be up to about 20 weight percent and is preferably between about 2 and 10 weight percent of the oral solid dosage form.

In accordance with one embodiment, the tablet has a disintegration time of 20 to 90 seconds in water at room temperature, about 25° C.±5° C. In accordance with an exemplary embodiment, the tablet has a disintegration time of 30 to 60 seconds in water at room temperature, about 25° C.±5° C. In accordance with an embodiment, the tablet has hardness of at least 3 Kp (Kilopond). In accordance with an exemplary embodiment, the tablet has hardness of 3 to 20 Kp.

Any conventional compression techniques well known to the person skilled in the art may be used to form the oral solid dosage form of the present disclosure.

The present disclosure also relates to a twin screw processor for preparing porous effervescent granules. The processor comprises an intake zone for receiving an input blend comprising an acid and a base; a granulation initiation zone for melting only a portion of the acid to serve as an in situ granulating agent; a granulation completion zone for granulating the input blend; and an outlet for discharging the granules.

Figure 2:
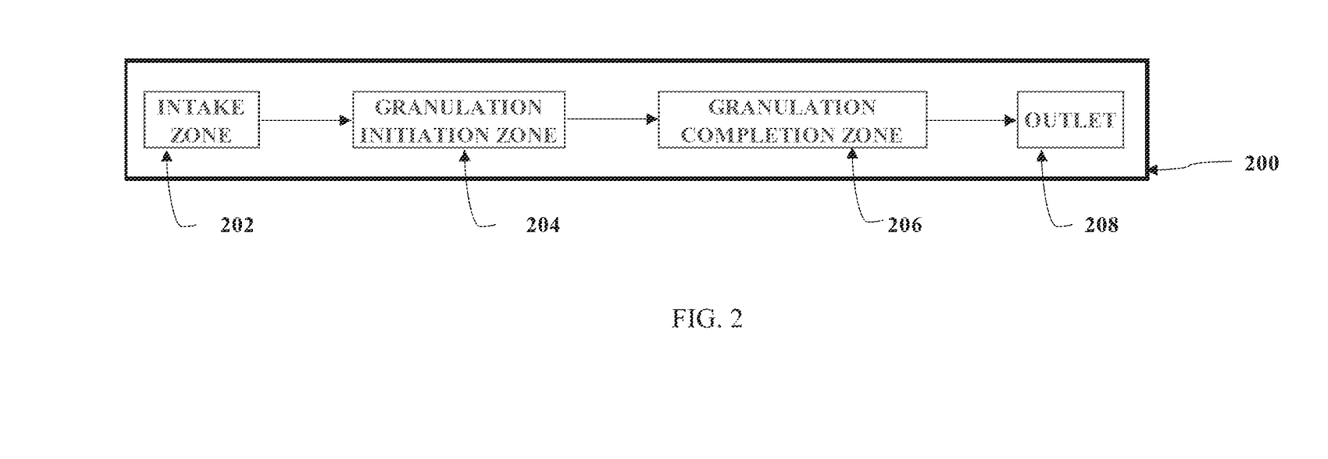
FIG. 2 illustrates a processor for manufacturing porous effervescent granules in accordance with an embodiment of the present disclosure.

FIG. 2 illustrates a processor (200) for preparing effervescent compositions in accordance with an embodiment of the present disclosure. The processor (200) comprises an intake zone (202) for receiving an input blend comprising an acid and a base, a granulation initiation zone (204) for melting only a portion of the acid to serve as an in situ granulating agent; a granulation completion zone (206) for granulating the input blend; and an outlet (208) for discharging the granules.

The granulation initiation zone of the processor is provided with heating elements to heat the processor barrel to a temperature sufficient to cause melting of only a portion of the acid. In some embodiments, the granulation initiation zone is maintained at a temperature 10 to 40° C. lower than the melting temperature of the acid. In an exemplary embodiment, the granulation initiation zone is maintained at a temperature about 20° C. lower than the melting temperature of the acid. In accordance with an embodiment, the melting of only a portion of the acid is ensured by low residence time in the granulation initiation zone. In accordance with an embodiment, the residence time in the processor is less than 10 seconds. In accordance with a specific embodiment, the residence time in the processor having an L/D of 60, is 8 to 10 seconds. In accordance with a specific embodiment, the residence time in the granulation initiation zone is 3 to 5 seconds. In some embodiments, the granulation initiation zone solely consists of conveying elements. In some embodiments, the granulation initiation zone consists essentially of conveying elements. Conveying elements are the elements that are used for transporting the material downstream in a processor without exerting any significant shear on the material. Conveying elements help in preventing material stagnation and providing low residence times.

In some embodiments, the granulation completion zone is maintained at around 25 to 35° C. In some embodiments, the granulation completion zone of the processor is also provided with conveying elements. In accordance with one embodiment, the granulation completion zone of the processor solely consists of conveying elements. In some embodiments, the granulation completion zone consists essentially of conveying elements.

In some embodiments, the processor can further comprise a transition zone between the granulation initiation zone and the granulation completion zone. The transition zone can also comprise heating elements. The temperature of the transition zone is less than that of the granulation initiation zone. In some embodiments, the transition zone is maintained at a temperature lower than that of the granulation initiation zone and higher than that of the granulation completion zone. In an exemplary embodiment, the transition zone is maintained at 50 to 70° C. In accordance with one embodiment, the transition zone of the processor consists of conveying elements or a mix of conveying and kneading elements. Kneading elements are the elements used to introduce shear energy to the material also thereby helping in mixing. Increasing the angle of the kneading elements results in decreasing the conveying ability of the elements. In an exemplary embodiment, forward conveying 45° angle is used.

Figure 1:
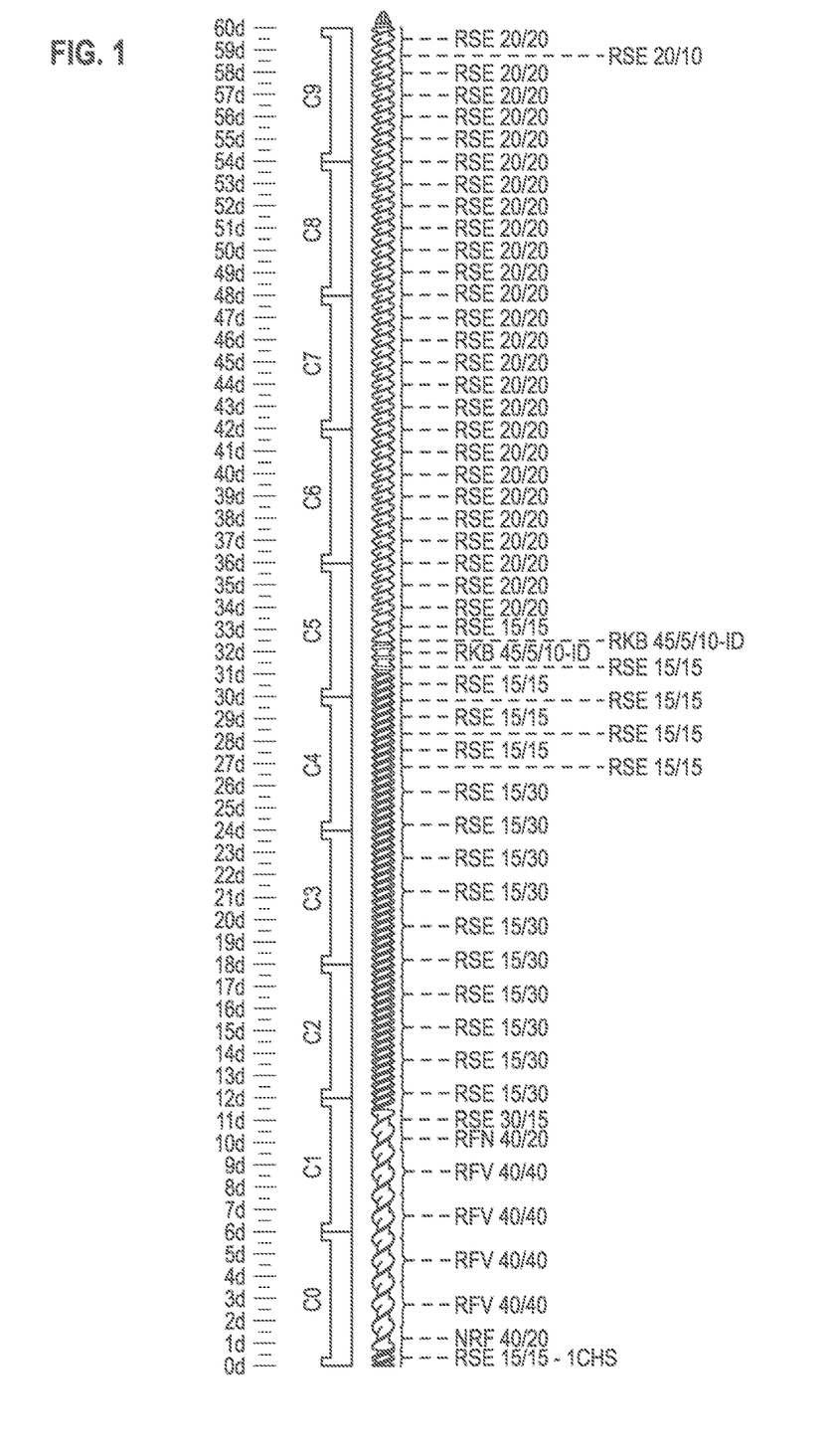
FIG. 1 illustrates the screw configuration of a co-rotating twin screw extruder in accordance with an embodiment of the present disclosure.

In some embodiments, the twin-screw processor is a co-rotating twin screw processor. In accordance with an embodiment, the co-rotating twin screw processor is a co-rotating twin screw extruder. The screw configuration of an exemplary co-rotating twin screw extruder is illustrated in FIG. 1.

The present disclosure also relates to a process for preparing a porous effervescent composition. In some embodiments, the process is used to make a porous effervescent composition that has porosity at least 50% greater than the porosity of the blend and which retains at least 90% $CO_2$ content of the input blend.

In some embodiments, the process comprises feeding an input blend comprising an acid and a base into a twin-screw processor, melting only a portion of the acid to serve as an in situ granulating agent, granulating the input blend to form granules, and optionally collecting the granules from the twin screw processor.

In some embodiments, melting of only a portion of the acid can be achieved by maintaining the granulation initiation zone at a temperature 10 to 40° C. lower than the melting temperature of the acid. In some embodiments, melting of only a portion of the acid can be achieved by maintaining low residence time within the processor such as within the granulation initiation zone of the processor. In some embodiments, melting of only a portion of the acid can be achieved by reducing the length of the granulation initiation zone. In some embodiments, the melting of only a portion of the acid can be achieved using a lower L/D ratio. In some embodiments, the L/D ratio is 60. The melting of only a portion of the acid can also be achieved by preventing material stagnation within the granulation initiation zone. In some embodiments, melting of only a portion of the acid is achieved by only using conveying elements within the granulation initiation zone. In some embodiments, melting of only a portion of the acid is achieved by essentially using conveying elements within the granulation initiation zone. Combinations of the embodiments can also be used to achieve the desired melting of only a portion of the acid. The melting of only a portion of the acid also minimizes any potential reactions between the acid and the base providing for a high amount (90 to 100%) of carbon dioxide retained in the effervescent granules.

In accordance with an embodiment, the melting of a portion of the acid includes surface melting of the acid. Surface melting is defined as the melting of that portion of the acid that is in physical contact with inner surface of the granulation initiation zone.

The portion of the acid that melts may be estimated using the torque observed in the processor and using it to calculate the power (P) and specific energy input (SEI). SEI is a measure of the energy that is input by the twin screw processor for producing the granules and can be in the form of thermal energy, mechanical energy and the like and combinations thereof. In accordance with an embodiment, the SEI can be a combination of thermal and mechanical energy. That is, $$SEI=SEI_{Mechanical}+SEI_{Thermal}$$

In accordance with another embodiment, the SEI can be substantially mechanical energy. In accordance with an embodiment, the SEI of the processor is less than the energy required for complete melting of the acid (Em). In accordance with an exemplary embodiment, the SEI of the processor can be about 50% of Em. An estimate of the percent of the acid melting can be obtained using the equation (1) as:

$$\text{Percent acid melted}=SEI/Em \times 100 \quad (1)$$

where the energy required for complete melting of acid (Em) can be obtained from a Differential Scanning calorimetry (DSC) thermogram of the input blend as well as its ingredients.

In accordance with an embodiment where SEI is substantially mechanical energy, the power (P) and specific energy input ($SEI_{mechanical}$) can be calculated using the equations (2) and (3):

$$P=2\pi N\tau/60,000 \quad (2)$$

where, P=Power (kW)
N=Screw Speed (rpm)
τ=Torque (Nm)

$$SEI_{mechanical}=\text{Power (kW)/through put or Feed rate (kg/h)} \quad (3)$$

where, $SEI_{mechanical}$ is Mechanical Specific Energy Input (kWh/kg) of the twin screw processor.

The input blend is processed and conveyed towards the outlet of the processor from the granulation initiation zone through a granulation completion zone. The processing and conveying allows the portion of the acid that has been melted to solidify, thereby achieving granulation within the processor. In some embodiments, only conveying elements or substantially conveying elements are used in a granulation completion zone of the processor. The granulation step aids in the formation of discrete free flowing granules with high porosity and compressibility. In some embodiments, the process of forming porous effervescent compositions using the twin screw processor can be a batch process. In some embodiments, the process of forming effervescent compositions using the twin screw processor can be a continuous process. The term "batch process" refers to a process where all materials are charged before the start of processing and are discharged at the end of processing. The term "continuous process" refers to a process where material is simultaneously charged and discharged during the processing.

In accordance with one embodiment, the input blend fed into the processor has moisture content of less than 0.5%.

IV. Overview Of Several Embodiments

The compositions, process and processor embodiments disclosed herein provide for the production of effervescent compositions having critical attributes such as higher porosity and higher carbon dioxide content as compared to conventional similar effervescent compositions. These porous effervescent compositions can be further processed using processing excipients to form, for example, effervescent tablets which exhibit improved mechanical strength, and also exhibit rapid disintegration times of generally less than 60 seconds.

The process embodiments disclosed do not require any additives, such as water, solvents, or affirmatively added binders. The process and processor embodiments disclosed herein also provide for a cost efficient continuous system. The process embodiments disclosed herein are scalable and suitable for rapid production of high volumes of effervescent compositions.

The melting of only a portion of the acid is believed to contribute towards achieving effervescent granules having a relative porosity of at least 50% and retained carbon dioxide content of at least. 90% of the input blend. In some embodiments, the composition has a normal particle size distribution wherein at least 90% of the particles are not greater than 1000 microns. Such a particle size distribution aids the free flowing nature of the granules. The melting of only a portion of the acid is also believed to contribute towards an increase in relative porosity of the granules. High porosity of the granules aids in rapid disintegration of the tablets. The melting of only a portion of the acid is also believed to contribute towards the formation of irregular granules that increases their compressibility thereby making the granules suitable for tableting resulting in the tablet having sufficient hardness for product handling and packaging activities. The tablets obtained from the granules of the present disclosure have a disintegration time of less than 60 seconds and hardness of at least 3 kp.

V. Examples

Described herein are examples for determining the moisture content, retained $CO_2$ content, disintegration time, porosity, bulk density and tap density and other properties of the porous effervescent composition, specifically granules, formed using embodiments of the claimed process. Some examples highlight the benefits of using the presently disclosed compositions and methods in comparison to conventional processes.

Exemplary processes used for measuring these properties are described below.

Determination of Moisture Content: The input blend and the granules were analyzed by an infrared moisture balance analyzer at 75° C. for 5 minutes. Loss in weight was recorded as percent (%) moisture content with respect to their initial weight.

Determination of Retained $CO_2$ Content: 5.0 g of input blend and 5.0 g of granules were added in two separate 100 ml 10% v/v sulfuric acid solutions. The loss in weight of the input blend and granules due to liberation of $CO_2$ as a result of the reaction between sulfuric acid and bicarbonate or carbonate present in the blend or granules was recorded as observed weight of carbon dioxide. The difference between the weight of the input blend and granules after reaction and the initial weight of input blend and granules respectively was calculated to measure the retained $CO_2$ content (g) in the blend or granules. The percent (%) relative retained $CO_2$ content in the granules was then calculated using the formula below:

Relative retained $CO_2$ content (%)=(Observed Weight (g) of $CO_2$ in granules×100)/Observed Weight (g) of $CO_2$ in input blend Determination of Disintegration Time of Effervescent Tablet: The disintegration time was calculated as the average time required for each of three effervescent tablets (number of units tested (n)=3) to disintegrate in 200 ml of purified water at room temperature, about 25° C.±5° C. and form a clear solution.

Determination of Hardness and Thickness of Effervescent Tablet: The hardness was calculated as the average of the hardness measured using Inweka TBH 125 hardness tester (Germany) for each of five effervescent tablets (number of units tested (n)=5). The thickness was calculated as the average of the thickness measured using vernier callipers for each of five effervescent tablets (number of units tested (n)=5).

Measurement of Bulk and Tap Density: A known amount (m) of the input blend and the granules were added into two separate dry graduated 100 ml cylinders. The contents of the two cylinders were leveled without compacting; and the unsettled apparent bulk volume ($V_0$) to the nearest graduated unit was read.

The bulk density (g/ml) was calculated using formula:

Bulk Density=Mass ($m$)/Bulk Volume ($V_0$)

To calculate the tap density, the contents of the two cylinders were tapped mechanically upto a maximum of 1250 taps and the apparent tapped volume ($V_t$) to the nearest graduated unit was read. The tap density was calculated using formula:

Tap Density=Mass ($m$)/Tapped Volume ($V_t$)

Measurement of porosity: Porosity was measured in terms of percentage relative bulk porosity and percentage relative tap porosity.

Percentage relative bulk porosity was calculated considering 1 g specific (Sp) volume using formula:

% Relative Bulk Porosity=((Bulk Sp. volume of 1 g granule−Bulk Sp. volume of 1 g input blend)×100)/Bulk Sp. volume of 1 g input blend Where, Bulk Sp. volume of 1 g granule=1/Bulk density of granules; and Bulk Sp. volume of 1 g input blend=1/Bulk density of input blend Percentage relative tap porosity was calculated considering 1 g specific (Sp) volume using formula:

% Relative Tap Porosity=((Tap Sp. volume of 1 g granule−Tap Sp. volume of 1 g input blend)×100))/Tap Sp. volume of 1 g input blend Where, Tap Sp. volume of 1 g granule=1/Tap density of granules Tap Sp. volume of 1 g input blend=1/Tap density of input blend Measurement of Compressibility: Compressibility was measured in terms of Hausner ratio and Compressibility Index, as provided in Hausner, H. H., Int. J. Powd. Metall, Vol 3, pg 7, 1967 and Carr, R. L., Chem. Eng., Vol 72, Issue 1, pg 163 and Issue 2, pg 69, 1965, respectively. Both the citations are incorporated herein by reference.

Example 1: Preparation of a Porous Effervescent Composition According to the Present Disclosure Four experiments were conducted to form exemplary granules with different acids. The ingredients used to form the exemplary granules are listed below.

TABLE 1

Ingredient for preparing Exemplary Effervescent Granules

| Exemplary Granule | Ingredients | Moles | % w/w |
|---|---|---|---|
| Exemplary Granules 1 | Citric acid anhydrous | 1.00 | 44.55 |
|  | Sodium bicarbonate | 2.58 | 50.28 |
|  | Anhydrous sodium carbonate | 0.21 | 5.16 |
| Exemplary Granules 2 | Malic acid | 1.00 | 45.70 |
|  | Sodium bicarbonate | 1.72 | 49.24 |
|  | Anhydrous sodium carbonate | 0.14 | 5.06 |
| Exemplary Granules 3 | Adipic acid | 1.00 | 47.84 |
|  | Sodium bicarbonate | 1.72 | 47.29 |
|  | Anhydrous sodium carbonate | 0.14 | 4.85 |
| Exemplary Granules 4 | Tartaric acid | 1.00 | 48.50 |
|  | Sodium bicarbonate | 1.72 | 46.69 |
|  | Anhydrous sodium carbonate | 0.14 | 4.79 |

To form the granules, each ingredient of the input blend was tray dried at 45° C. to reduce their moisture content to less than 0.5% w/w followed by sifting of each ingredient separately through ASTM #60 mesh sieve. The sifted ingredients were mixed in a cone blender to form an input blend. The input blend was processed immediately in a co-rotating twin screw extruder. The machine specification and the process parameters are described in Table 2, below:

TABLE 2

Machine specification and the process parameters

| | |
|---|---|
| Machine Name | Omega 20 |
| Total no. of Barrels | 10 |
| Barrel Diameter | 20 mm |
| Length of Each Barrel | 120 mm |
| Total Length of Barrels | 1200 mm |
| Machine Length to Diameter Ratio (L/D) | 60 |
| Screw Configuration | Please see FIG. 1 |
| Screw Speed | 600 rpm |
| Processing Area Temperature | 25° C.-35° C. |
| Processing area Relative Humidity (%) | 20 ± 5% |
| Residence time* | 8-10 seconds |
| Element length | 1200 mm |
| Maximum Screw Speed | 1000 rpm |
| Maximum motor power | 9 KW |
| Diameter | 19.6 mm |
| Percentage of kneading blocks | 1.6 |

Screw Elements

| | |
|---|---|
| 1. | RSE 15/15-1CHS |
| 2. | NRF 40/20 |
| 3. | RFV 40/40 |
| 4. | RFV 40/40 |
| 5. | RFV 40/40 |
| 6. | RFV 40/40 |
| 7. | RFN 40/20 |
| 8. | RSE 30/15 |
| 9. | RSE 15/30 |
| 10. | RSE 15/30 |
| 11. | RSE 15/30 |
| 12. | RSE 15/30 |
| 13. | RSE 15/30 |
| 14. | RSE 15/30 |
| 15. | RSE 15/30 |
| 16. | RSE 15/30 |
| 17. | RSE 15/30 |
| 18. | RSE 15/30 |
| 19. | RSE 15/15 |
| 20. | RSE 15/15 |
| 21. | RSE 15/15 |
| 22. | RSE 15/15 |
| 23. | RSE 15/15 |
| 24. | RSE 15/15 |
| 25. | RSE 15/15 |
| 26. | RKB 45/5/10 |
| 27. | RKB 45/5/10 |
| 28. | RSE 15/15 |
| 29. | RSE 20/20 |
| 30. | RSE 20/20 |
| 31. | RSE 20/20 |
| 32. | RSE 20/20 |
| 33. | RSE 20/20 |
| 34. | RSE 20/20 |
| 35. | RSE 20/20 |
| 36. | RSE 20/20 |
| 37. | RSE 20/20 |
| 38. | RSE 20/20 |
| 39. | RSE 20/20 |
| 40. | RSE 20/20 |
| 41. | RSE 20/20 |
| 42. | RSE 20/20 |
| 43. | RSE 20/20 |
| 44. | RSE 20/20 |
| 45. | RSE 20/20 |
| 46. | RSE 20/20 |
| 47. | RSE 20/20 |
| 48. | RSE 20/20 |
| 49. | RSE 20/20 |
| 50. | RSE 20/20 |
| 51. | RSE 20/20 |
| 52. | RSE 20/20 |
| 53. | RSE 20/20 |
| 54. | RSE 20/10 |
| 55. | RSE 20/20 |

*Residence time (RT) is defined as the time duration of the material spent within the processor. RT can be affected by feed rate, screw speed, free volume of the processor and density of the material.

List of Abbreviations for Elements

| | |
|---|---|
| RSE | Right Handed Screw Element |
| RFV | Regular Flight Shovel Element |
| RIN | Regular Flight Shovel Element to Normal |
| RKB | Right Handed Kneading Block |
| NRF | Normal to RFV (transition element) |
| CHS | Champer and Step |

While the aforementioned parameters were kept constant for the four experiments, the feed rate and the barrel temperature profile were varied as mentioned below.

Feed Rate: Feed rate was maintained at 186 grams/minute for citric acid; 205 grams/minute for malic acid; 225 grams/minute for adipic acid and 215 grams/minute for tartaric acid.

Barrel Temperature Profile for Exemplary Granules formed Using Different Acids: Please refer to Table 3 provided below.

TABLE 3

Barrel Temperature Profile

| | Barrel No. | | | | | | | | | |
|---|---|---|---|---|---|---|---|---|---|---|
| | C0 Feeding Zone | C1 | C2 Granulation Initiation Zone | C3 | C4 | C5 Transition Zone | C6 Granulation Completion Zone | C7 | C8 | C9 |
| Temp. (° C. ±10° C.) - Citric Acid | 30 | 30 | 130 | 130 | 130 | 60 | 30 | 30 | 30 | 30 |
| Temp. (° C. ±10° C.) - Malic Acid | 30 | 30 | 120 | 120 | 120 | 60 | 30 | 30 | 30 | 30 |
| Temp. (° C. ±10° C.) - Adipic Acid | 30 | 30 | 140 | 140 | 140 | 60 | 30 | 30 | 30 | 30 |
| Temp. (° C. ±10° C.) - Tartaric Acid | 30 | 30 | 150 | 150 | 150 | 60 | 30 | 30 | 30 | 30 |

The granules obtained from the outlet of the co-rotating twin screw extruder were tray dried at 45° C. until the loss on drying was less than 0.5% w/w; and stored in a moisture proof packing. The granules were then assessed to determine their properties. The properties of the granules obtained in the four experiments have been summarized in Table 4, below.

TABLE 4

Properties of the effervescent granules

| Parameters | Exemplary Granules 1 Containing Citric Acid | | Exemplary Granules 2 Containing Malic Acid | | Exemplary Granules 3 Containing Adipic Acid | | Exemplary Granules 4 Containing Tartaric Acid | |
| --- | --- | --- | --- | --- | --- | --- | --- | --- |
| | Input Blend | Granules | Input Blend | Granules | Input Blend | Granules | Input Blend | Granules |
| Moisture Content (% w/w) | 0.17 | 0.51 | 0.19 | 0.26 | 0.25 | 0.34 | 0.18 | 0.45 |
| Observed Weight of $CO_2$ (g) | 1.43 | 1.36 | 1.40 | 1.35 | 1.38 | 1.28 | 1.32 | 1.31 |
| Relative retained $CO_2$ content of Granules (%)** | — | 95.10 | — | 97.82 | — | 92.75 | — | 99.24 |
| Bulk Density (g/cc$^3$) | 0.680 | 0.389 | 0.762 | 0.464 | 0.832 | 0.488 | 0.794 | 0.52 |
| Tap Density (g/cc$^3$) | 1.137 | 0.555 | 1.005 | 0.633 | 1.040 | 0.661 | 1.118 | 0.739 |
| Compressibility index (%) | 40.00 | 30.0 | 24.14 | 26.67 | 20.0 | 26.15 | 29.03 | 29.23 |
| Hausner ratio | 1.667 | 1.429 | 1.320 | 1.364 | 1.250 | 1.354 | 1.408 | 1.413 |
| Relative Specific Bulk Porosity (%) | — | 74.81 | — | 64.25 | — | 70.49 | — | 51.82 |
| Relative Specific Tap Porosity (%) | — | 104.86 | — | 58.77 | — | 57.34 | — | 51.29 |
| Median Particle diameter (μm) | — | 480 | — | 700 | — | 630 | — | 350 |
| Particles retained on ASTM # 60 mesh sieve (%) | — | 87.43 | — | 83.12 | — | 82.31 | — | 74.15 |

**Note:
Due to random error in measurement, the value of retained $CO_2$ content may vary between +5% and may also exceed 100.

As an example, the calculation of % relative retained $CO_2$ content for Exemplary Granules 1 containing Citric acid is shown below:

% relative retained $CO_2$ content=(Observed Weight (g) of $CO_2$ in granules×100)/Observed Weight (g) of $CO_2$ in input blend The values in Table 4 when placed in the equation above yield the following value:

% relative retained $CO_2$ content=(1.36×100)/1.43=95.10

As an example, the calculation of % relative specific bulk porosity for Exemplary Granules 1 containing Citric acid is shown below:

Bulk Sp. volume of 1 g granules=1/Bulk density of granules

Bulk Sp. volume of 1 g input blend=1/Bulk density of input blend

% Relative Bulk Porosity=((Bulk Sp. volume of 1 g granules−Bulk Sp. volume of 1 g input blend)× 100))/Bulk Sp. volume of 1 g input blend The values in Table 4 when placed in the equation above yield the following value:

Bulk Sp. volume of 1 g granule=1/0.389=2.570

Bulk Sp. volume of 1 g input blend=1/0.680=1.470%

Relative Bulk Porosity=(2.57−1.47×100)/1.47=74.81

As an example, the calculation of % relative Specific Tap Porosity for Exemplary Granules 1 containing Citric acid is shown below:

Tap Sp. volume of 1 g granules=1/Tap density of granules

Tap Sp. volume of 1 g input blend=1/Tap density of input blend

% Relative Tap Porosity=((Tap Sp. volume of 1 g granules−Tap Sp. volume of 1 g input blend)× 100))/Tap Sp. volume of 1 g input blend The values in Table 4 when placed in the equation above yield the following value:

Tap Sp. volume of 1 g granules=1/0.555=1.801

Tap Sp. volume of 1 g input blend=1/1.137=0.879%

Relative Tap Porosity=(1.801−0.879×100)/0.879=104.86

Observations: The % relative retained $CO_2$ content was found to be greater than 90% and the relative specific bulk porosity as well as relative specific tap porosity of the granules was found to be greater than 50%.

Example 2: Preparation of Exemplary Effervescent Tablets

The exemplary granules 1-4 obtained in the four experiments described in Example 1 were maintained at 45° C. till the loss on drying was 0.5% w/w. The dried granules were passed through ASTM mesh #20 sieve. The granules from the above step were compressed into tablets weighing 2.5 grams using a single station table top Inweka tablet compression machine (Ahmedabad, India) with 20 mm round flat faced bevel edge tooling. The tablets were then assessed to determine their properties. The properties of the tablets obtained in the four experiments have been summarized in Table 5, below.

TABLE 5

Properties of Tablets obtained using
the Exemplary Effervescent Granules

| Effervescent Tablet Obtained Using Acid | Hardness (Kiloponds) (n = 5) | Disintegration Time (in seconds) (n = 3) |
|---|---|---|
| Citric Acid | 9.4 | 35 |
| Malic Acid | 6.3 | 30 |
| Adipic Acid | 6.4 | 55 |
| Tartaric Acid | 3.3 | 90 |

Observation: The tablets were observed to have hardness of at least 3 Kp with a disintegration time between 20 and 90 seconds.

Example 3: Preparation of Effervescent Tablets with API

Three experiments were conducted to form effervescent tablets comprising the APIs—Aspirin, N-Acetyl-L-Cysteine (NAC) and Cefixime. The ingredients used to form the effervescent tablets are provided below.

TABLE 6

Ingredients for Preparing Effervescent Tablets comprising an API

| Tablets | Ingredients | % w/w |
|---|---|---|
| Tablet 1: 325 mg of aspirin in 4.06 g tablet | Aspirin | 8.00 |
| | Exemplary Granules 1 | 86.15 |
| | Sucralose | 0.80 |
| | Strawberry Flavor | 0.05 |
| | Sodium benzoate | 5.00 |
| Tablet 2: 450 mg of N-acetyl-L-cysteine (NAC) in 2.5 g tablet | NAC | 18.00 |
| | Exemplary Granules 1 | 76.15 |
| | Sucralose | 0.80 |
| | Strawberry Flavor | 0.05 |
| | Sodium benzoate | 5.00 |
| Tablet 3: 200 mg of of Cefixime in 2.0 g tablet | Cefixime Trihydrate | 10.00 |
| | Exemplary Granules 1 | 84.15 |
| | Sucralose | 0.80 |
| | Strawberry Flavor | 0.05 |
| | Sodium benzoate | 5.00 |

To form the effervescent tablets 1, 2 and 3 having composition mentioned in Table 6 above, the Exemplary Granules 1 prepared in accordance with Example 1 was passed through ASTM #30 mesh sieve. The API was separately sieved through ASTM #30 mesh sieve. The Exemplary Granules 1 and the API thus obtained were mixed manually. Other ingredients (sucralose and strawberry flavour) were passed through ASTM #60 mesh sieve and then mixed with the mixture obtained above. The final mixture was lubricated with sodium benzoate that has been passed through ASTM #60 mesh sieve. The lubricated mixture was compressed into tablets using a single station table top Inweka tablet compression machine (Ahrnedabad, India) with 20 mm round flat face bevel edge tooling.

The effervescent tablets thus obtained were then assessed to determine their properties. The properties of the tablets obtained in the three experiments have been summarized in Table 7, below.

TABLE 7

Properties of the Effervescent Tablets

| Property | Tablets of Asprin | Tablets of NAC | Tablets of Cefixime |
|---|---|---|---|
| Thickness (mm) (n = 5) | 9.80 | 6.20 | 4.93 |
| Hardness (Kp) (n = 5) | 7.0 | 6.1 | 5.7 |
| Disintegration time (Seconds) (n = 3) | 36 | 26 | 25 |

Observations: The tablets were observed to have hardness of at least 5 Kp with disintegration time of as low as 25 seconds.

Example 4: Preparation of Effervescent Granules by Using Meltable Binder as an Affirmatively Added Granulating Agent In one example, tablets were made using a process wherein an affirmatively added binder was used to form granules. The ingredients used to form the tablets in this example are provided below.

TABLE 8

Ingredients for preparing granules using a process involving use of an affirmatively added binder

| S. No. | Ingredients | % w/w |
|---|---|---|
| 1 | Citric acid anhydrous | 40.09 |
| 2 | Sodium bicarbonate | 45.26 |
| 3 | Sodium carbonate anhydrous | 4.65 |
| 4 | Xylitol (affirmatively added binder) | 10.00 |
| | Total | 100.00 |

Each ingredient was tray dried at 45° C. to reduce the moisture content less than 0.5% w/w and sifted separately through ASTM #60 mesh sieve. The dispensed ingredients were mixed manually and processed immediately as per the processing conditions mentioned below using a co-rotating twin screw extruder. The machine specification and the process parameters are described in Table 9, below:

TABLE 9

Machine specifications and processing conditions

| 1 | Machine | Omega 20 |
|---|---|---|
| 2 | Barrel Diameter | 20 mm |
| 3 | Each Barrel length | 120 mm |
| 4 | Total no. of Barrels | 10 nos. |
| 5 | Total Length of Barrel | 1200 mm |
| 6 | Machine L/D | 60 |
| 7 | Screw Speed | 600 rpm |
| 8 | Screw Configuration | Please see FIG. 1 |
| 9 | Feed Rate | 10 Hz (215 grams/minute) |
| 10 | Barrel temperature Profile | As illustrated in Table 10 |

The process was carried out in a twin screw extruder having the novel screw configuration and elements as used in the disclosed process.

TABLE 10

| Barrel temperature Profile | | | | | | | | | | |
|---|---|---|---|---|---|---|---|---|---|---|
| | Barrel No. | | | | | | | | | |
| | C0 | C1 | C2 | C3 | C4 | C5 | C6 | C7 | C8 | C9 |
| Temperature (° C. ±10° C.) | 30 | 30 | 100 | 100 | 100 | 60 | 30 | 30 | 30 | 30 |

The granules thus obtained were tray dried at 45° C. until the moisture content was less than 0.5% w/w and stored in moisture proof packing. The granules were then assessed to determine their properties. The properties of the granules have been summarized in Table 11, below.

TABLE 11

| Properties of granules | |
|---|---|
| Parameters | Granules |
| Relative retained $CO_2$ content of granules (%) | 84.74 |
| Bulk Density (g/cc3) | 0.463 |
| Relative % bulk porosity | 15 |

Observations: The $CO_2$ content efficiency for granules made using the above method was found to be much lower than that obtained using the teachings of the present disclosure. Lower content of $CO_2$ likely is attributable to loss in $CO_2$ due to the reaction between the acid and the base. It is envisaged that any additional elements such as kneading elements if added to the granulation initiation zone will not yield satisfactory granules.

In view of the many possible embodiments to which the principles of the present disclosure may be applied, it should be recognized that the illustrated embodiments are only preferred examples of the present disclosure and should not be taken as limiting the scope of the presently disclosed subject matter. Rather, the scope of the present disclosure is defined by the following claims.

Specific Embodiments are Described Below

A granular composition comprising an anhydrous acid component comprising a combination of a portion of the acid that has been melted and a portion of the acid that has not been melted and; an anhydrous base component comprising a carbonate functional group, wherein the base component is capable of reacting with the acid component to form carbon dioxide; and wherein the anhydrous acid component and the anhydrous base component are present in a weight ratio ranging from 1:9 to 9:1 and the composition does not comprise an affirmatively added granulating agent.

Such composition(s), wherein the composition further comprises an active pharmaceutical agent selected from a group consisting of an anti-infective, an antibacterial, an antihistamine, a decongestant, an antiinflammatory, an antiparasitic, an antiviral, an antifungal, an amoebicidal, a trichomonocidal agent, an analgesic, an antiarthritic, an antiasthmatic, an anticoagulant, an anticonvulsant, an antidepressant, an antidiabetic, an antineoplastic, an antipsychotic, an antihypertensive, an expectorant, an electrolyte, a laxative, a phytopharmaceutical, a muscle relaxant, a diuretic, or combinations thereof.

Such composition(s), wherein the composition further comprises aspirin, N-Acetyl-L-Cysteine, Cefixime, or a combination thereof.

A porous effervescent composition formed from an input blend comprising an acid and a base by granulating the input blend in a twin-screw processor, the porous effervescent composition formed by an in situ granulating agent, wherein the in situ granulating agent is a portion of the acid, the portion of the acid being a portion of the acid that melts during granulation.

Such composition(s), wherein the porous effervescent composition has porosity at least 50% greater than the porosity of the input blend.

Such composition(s), wherein the porous effervescent composition has retained carbon dioxide content of at least 90% of the input blend.

Such composition(s), wherein the composition does not contain, or is free of, an affirmatively added granulating agent.

Such composition(s), wherein one or both of the acid and the base of the input blend is anhydrous.

Such composition(s), wherein the input blend has moisture content of less than 0.5% w/w of the composition.

Such composition(s), wherein the acid is selected from a group consisting of citric acid, tartaric acid, adipic acid, malic acid, or combinations thereof.

Such composition(s), wherein the input blend further comprises one or more ingredients selected from a group consisting of pharmaceutical, food, veterinary, nutraceutical, horticultural, household, culinary, pesticidal, agricultural, cosmetic, herbicidal, industrial, cleansing, confectionery and flavoring agents, or combinations thereof.

Such composition(s), wherein the input blend further comprises one or more processing excipients selected from a group consisting of soluble and insoluble lubricants, flavoring substances, coloring agents, or combinations thereof.

An oral solid dosage form comprising a porous effervescent composition formed from an input blend comprising an acid and a base by granulating the input blend in a twin-screw processor, the porous effervescent composition comprising granules formed by an in situ granulating agent, wherein the in situ granulating agent is a portion of the acid, the portion of the acid being a portion of the acid that melts during granulation; and one or more optional processing excipients.

Such form(s), wherein one or both of the acid and the base of the input blend is anhydrous.

Such form(s), wherein the porous effervescent composition has porosity at least 50% greater than the porosity of the input blend.

Such form(s), wherein the porous effervescent composition has a percent retained carbon dioxide content of at least 90% of the input blend.

Such form(s), wherein the acid is selected from a group consisting of citric acid, tartaric acid, adipic acid, malic acid, or combinations thereof.

Such form(s), further comprising one or more ingredients selected from a group consisting of pharmaceutical, food, veterinary, nutraceutical, horticultural, household, culinary, pesticidal, agricultural, cosmetic, herbicidal, industrial, cleansing, confectionery and flavoring agents, or combinations thereof.

Such form(s), wherein the processing excipients are selected from a group consisting of from non-effervescent disintegrants, soluble and insoluble lubricants, flavoring substances, coloring agents, or combinations thereof.

Such form(s), wherein the oral solid dosage form is selected from a group consisting of an effervescent tablet, a powder for oral administration, or a combination thereof.

Such form(s), wherein the effervescent tablet is a rapidly disintegrating tablet or an orally disintegrating tablet.

Such form(s), wherein the effervescent tablet has a disintegration time of 20 to 90 seconds in water at room temperature of about 25° C.±5° C.

Such form(s), wherein the effervescent tablet has hardness of at least 3 Kp.

A process for preparing porous effervescent granules, the process comprising feeding an input blend comprising an acid and a base into a twin-screw processor; melting only a portion of the acid to serve as an in situ granulating agent; granulating the input blend to form granules; and optionally collecting the granules from the twin screw processor granulating the input blend to form granules.

Such process(es), wherein the melting of only a portion of the acid is achieved in a granulation initiation zone of the twin screw processor without any material stagnation, the granulation initiation zone consisting essentially of conveying elements.

Such process(es), wherein the melting of only a portion of the acid is achieved by keeping low residence time within the twin-screw processor.

Such process(es), wherein the melting of only a portion of the acid is achieved by keeping low residence time within the granulation initiation zone of the twin-screw processor.

Such process(es), wherein the granulation initiation zone is maintained at a temperature sufficient to cause melting of only a portion of the acid.

Such process(es), wherein specific input energy of the twin screw processor is less than the energy required for completely melting the acid.

Such process(es), wherein the twin-screw processor is a co-rotating twin screw extruder.

Such process(es), wherein the granules collected from the twin screw processor have porosity at least 50% greater than the porosity of the input blend.

Such process(es), wherein the granules collected from the twin screw processor have retained carbon dioxide content of at least 90% of the input blend.

Such process(es), wherein the process is a continuous process or a batch process.

A twin screw processor for preparing porous effervescent granules, the twin-screw processor comprising an intake zone for receiving an input blend comprising an acid and a base; a granulation initiation zone for melting a portion of the acid to serve as an in situ granulating agent; a granulation completion zone for granulating the input blend; and
 an outlet for discharging the granules.

Such processor(s), wherein the granulation initiation zone consists essentially of conveying elements.

Such processor(s), wherein the granulation initiation zone comprises heating elements to maintain the granulation initiation zone at a temperature sufficient to melt only a portion of the acid.

Such processor(s), wherein the granulation completion zone consists essentially of conveying elements.

Such processor(s), wherein the granulation completion zone is maintained at a temperature lower than that of the granulation initiation zone.

Such processor(s), further comprising a transition zone between the granulation initiation zone and the granulation completion zone, the transition zone maintained at a temperature lower than that of the granulation initiation zone and higher than that of the granulation completion zone.

Such processor(s), wherein the twin-screw processor is a co-rotating twin screw extruder.

Porous effervescent granules comprising an acid and a base, wherein the porous effervescent granules have porosity at least 50% greater than the porosity of an input blend used to prepare the granules and the granules retain at least 90% of carbon dioxide of the input blend.

A composition, comprising a carbonate-containing base; and a combination of melted acid and un-melted acid, the combination configured to increase the porosity of the composition by at least 50%.

A composition, comprising a carbonate-containing base; and a combination of melted acid and un-melted acid, the combination configured to retain at least 90% of carbon dioxide.

A porous effervescent composition formed from an input blend comprising an acid and a base by granulating the input blend in a twin-screw processor, the porous effervescent composition comprising granules formed by an in situ granulating agent, wherein the in situ granulating agent is a portion of the acid, the portion of the acid being a portion of the acid that melts during granulation and where the specific input energy of the twin screw processor does not exceed 50% of the energy required for completely melting the acid.

We claim:

1. An effervescent granular composition comprising:
   a plurality of discrete free flowing granules that have a particle size distribution such that a size of at least 90% of the plurality of discrete free flowing granules is not greater than 1000 microns, wherein each granule of the plurality of discrete free flowing granules is irregularly shaped and comprises:
   an anhydrous acid component; and
   an anhydrous base component comprising a carbonate functional group, wherein:
   the anhydrous base component is capable of reacting with the anhydrous acid component to form carbon dioxide;
   the anhydrous acid component and the anhydrous base component are present in a weight ratio ranging from 1:9 to 9:1;
   the anhydrous acid component consists of in situ granulating agent and unmelted acid;
   the in situ granulating agent is a portion of the anhydrous acid component that has been melted during granulation;
   the unmelted acid is a portion of the anhydrous acid component that has not been melted during granulation;
   the composition does not contain a granulating agent or a binder other than the in situ granulating agent; and
   the composition contains only one acid as the anhydrous acid component.

2. The composition of claim 1, wherein each irregularly shaped granule is formed by a granulation process that comprises:
   feeding an input blend comprising particles of the anhydrous acid component and particles of the anhydrous base component into a twin-screw processor such that a residence time of the input blend in the twin-screw processor is less than 10 seconds.

3. The composition of claim 1, wherein each irregularly shaped granule is formed by a granulation process that comprises:
   feeding an input blend comprising particles of the anhydrous acid component and particles of the anhydrous base component into a twin-screw processor such that a residence time of the input blend in a granulation initiation zone of the twin-screw processor is 3 to 5 seconds.

4. The composition of claim 1, wherein the composition is prepared by a process comprising:
   feeding an input blend comprising the anhydrous acid component and the anhydrous base component into a twin-screw processor;
   melting only a portion of the anhydrous acid component to serve as the in situ granulating agent by maintaining a residence time of the input blend in heated granulation initiation zone from 3 to 5 seconds;
   granulating the input blend to form the plurality of discrete free flowing granules; and
   collecting the plurality of discrete free flowing granules from the twin-screw processor,
   wherein the twin-screw processor comprises:
   an intake zone for receiving the input blend;
   a granulation initiation zone provided with heating elements to heat an inner surface of the granulation initiation zone; and
   a granulation completion zone, which is maintained at a temperature lower than that of the granulation initiation zone, for granulating the input blend.

5. The composition of claim 1, wherein the composition further comprises an active pharmaceutical agent selected from the group consisting of an anti-infective, an antibacterial, an antihistamine, a decongestant, an antiinflammatory, an antiparasitic, an antiviral, an antifungal, an amoebicidal, a trichomonocidal agent, an analgesic, an antiarthritic, an antiasthmatic, an anticoagulant, an anticonvulsant, an antidepressant, an antidiabetic, an antineoplastic, an antipsychotic, an antihypertensive, an expectorant, an electrolyte, a laxative, a phytopharmaceutical, a muscle relaxant, a diuretic, and a combination thereof.

6. The composition of claim 1, wherein the one acid is citric acid, tartaric acid, adipic acid, or malic acid.

7. The composition of claim 1, wherein the composition is not a taffy mass.

8. An oral solid dosage form comprising the composition of claim 1 and one or more excipients.

9. The oral solid dosage form of claim 8, wherein the oral solid dosage form is a tablet that has a disintegration time of 20 to 90 seconds in water at a temperature of 25° C.±5° C.

10. The oral solid dosage form of claim 8, wherein the oral solid dosage form is a tablet that has a hardness of at least 3 Kp.

11. A process for preparing the composition of claim 1, comprising:
   feeding an input blend comprising the anhydrous acid component and the anhydrous base component into a twin-screw processor;
   melting only a portion of the anhydrous acid to serve as the in situ granulating agent, and not melting a portion of the anhydrous acid component to serve as the unmelted acid;
   granulating the input blend to form the plurality of discrete free flowing granules; and
   collecting the plurality of discrete free flowing granules from the twin-screw processor.

\* \* \* \* \*